(12) United States Patent
Takahashi

(10) Patent No.: US 8,456,229 B2
(45) Date of Patent: Jun. 4, 2013

(54) FILTER DEVICE

(75) Inventor: Yusuke Takahashi, Nagano (JP)

(73) Assignee: Seiko Epson Corporation, Tokyo (JP)

( * ) Notice: Subject to any disclaimer, the term of this patent is extended or adjusted under 35 U.S.C. 154(b) by 0 days.

(21) Appl. No.: 13/414,150

(22) Filed: Mar. 7, 2012

(65) Prior Publication Data

US 2012/0229201 A1  Sep. 13, 2012

(30) Foreign Application Priority Data

Mar. 10, 2011  (JP) ................................. 2011-052611

(51) Int. Cl.
*H03B 1/10* (2006.01)
*H03K 5/00* (2006.01)
*H04B 1/10* (2006.01)

(52) U.S. Cl.
USPC .......................................... 327/551; 600/500

(58) Field of Classification Search
USPC .......................................... 327/551; 600/500
See application file for complete search history.

(56) References Cited

U.S. PATENT DOCUMENTS

| | | | |
|---|---|---|---|
| 4,222,266 A | * | 9/1980 | Theodoulou .................... 73/179 |
| 4,223,556 A | * | 9/1980 | Hutchins ......................... 73/179 |
| 2007/0060827 A1 | | 3/2007 | Kobayashi et al. |
| 2010/0198087 A1 | | 8/2010 | Takahashi et al. |
| 2011/0098582 A1 | | 4/2011 | Takahashi et al. |

FOREIGN PATENT DOCUMENTS

| | | |
|---|---|---|
| JP | 2007-054471 A | 3/2007 |
| JP | 2010-172645 A | 8/2010 |
| JP | 2011-087838 A | 5/2011 |
| JP | 2011-092236 A | 5/2011 |
| JP | 2011-212383 A | 10/2011 |
| JP | 2011-212384 A | 10/2011 |

* cited by examiner

*Primary Examiner* — Quan Tra
(74) *Attorney, Agent, or Firm* — Global IP Counselors, LLP

(57) ABSTRACT

A filter device includes a filter that separates a steady component and a non-steady component included in an input signal, a synthesis unit that synthesizes the separated steady component and the separated non-steady component according to a given ratio, and an evaluation unit that evaluates the magnitude of the amount of the non-steady component in the input signal, wherein the synthesis unit sets the given ratio to a first ratio in an instance in which the evaluation unit determines the amount of the non-steady component to be equal to or less than a predetermined reference, and sets the given ratio to a second ratio, in which the proportion of the non-steady component is less than that of the first ratio, in an instance in which the evaluation unit determines the amount of the non-steady component to be greater than the predetermined reference.

8 Claims, 7 Drawing Sheets

(EXAMPLE IN WHICH TEST SUBJECT IS IN STATE OF REST)

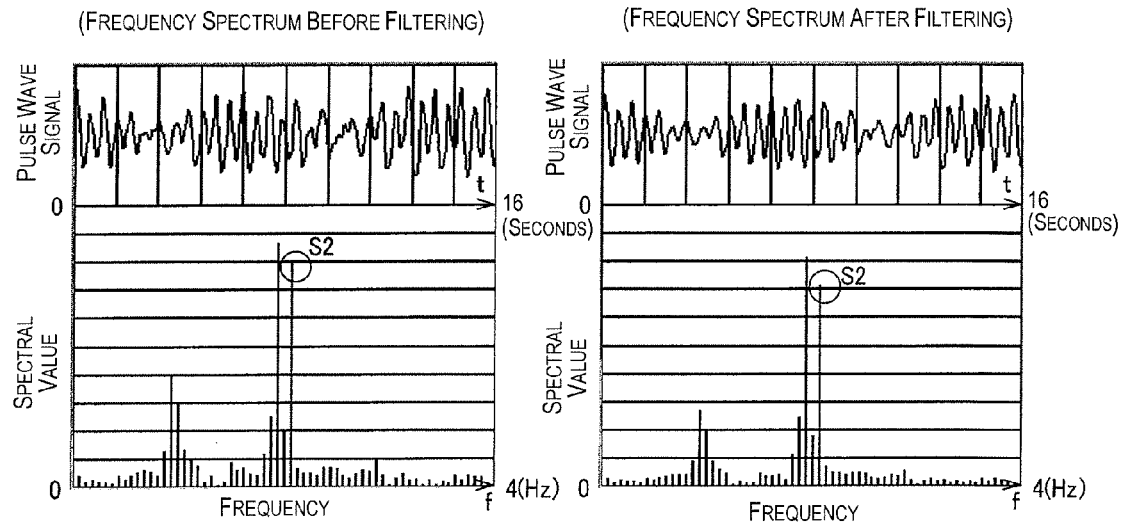
Fig. 6A Fig. 6B
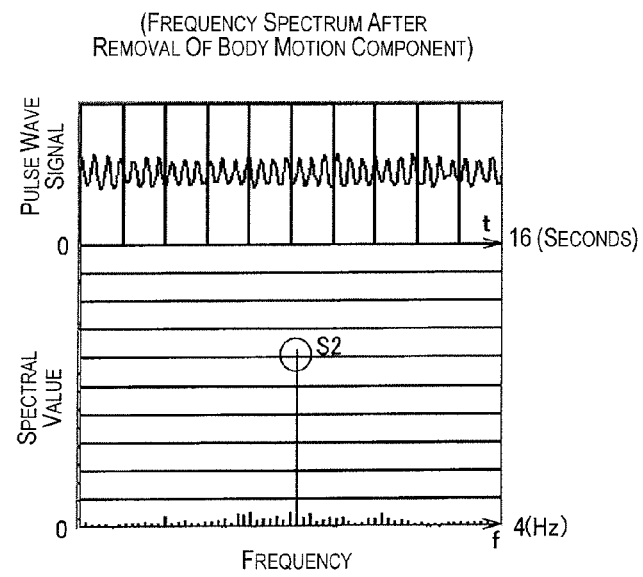
Fig. 6C

FILTER DEVICE

CROSS-REFERENCE TO RELATED APPLICATIONS

This application claims priority to Japanese Patent Application No. 2011-052611 filed on Mar. 10, 2011. The entire disclosure of Japanese Patent Application No. 2011-052611 is hereby incorporated herein by reference.

BACKGROUND

1. Technological Field

The present invention relates to a filter device and similar devices.

2. Background Technology

In, for example, a pulsation detection device for detecting a pulsation signal originating from pulsation in a test subject, a filtering process is performed by a filter device as a pre-process for detecting the pulsation signal. A signal inputted into the filter device is a pulse wave signal including, e.g., a pulsation signal, which is a steady component; and a body motion component originating from disturbance noise and the body motion of the test subject, which is a non-steady component.

A technology for filtering and thereby removing the noise component included in the pulse wave signal is described in, e.g., Patent Citation 1. In the technique described in Patent Citation 1, a band pass filter that passes a signal having a frequency near a frequency representing the pulse at that point in time is selected from a plurality of band pass filters.

Japanese Laid-open Patent Publication No. 2007-54471 (Patent Document 1) is an example of the related art.

SUMMARY

Problems to Be Solved by the Invention

In the technique described in Patent Citation 1, a band pass filter that passes a signal having a frequency near a frequency representing the pulse at that point in time is selected from a plurality of band pass filters. However, in order to realize such a process, it is necessary to, e.g., perform a large number of determining processes using software, meaning that the processing load will increase and the time required for processing will also increase.

According to at least one aspect of the invention, it is possible to, e.g., enhance the filter performance while reducing the processing load of the filter device.

Means Used to Solve the Above-Mentioned Problems (1) According to a first aspect of a filter device of the invention, the filter device includes: a filter that separates a steady component and a non-steady component included in an input signal, the filter being an adaptive filter in which updating of a filter coefficient causes frequency response characteristics to adapt in an autonomous fashion; a synthesis unit that synthesizes the separated steady component and the separated non-steady component according to a given ratio; and an evaluation unit that evaluates, on the basis of a result of a frequency analysis performed on at least one of the input signal, the separated steady component, and the separated non-steady component, the magnitude of the amount of the non-steady component included in the input signal; wherein the synthesis unit sets the given ratio to a first ratio in an instance in which the evaluation unit determines the amount of the non-steady component to be equal to or less than a predetermined reference, and sets the given ratio to a second ratio, in which the proportion of the non-steady component is less than that of the first ratio, in an instance in which the evaluation unit determines the amount of the non-steady component to be greater than the predetermined reference.

In the aspect described above, the adaptive filter separates the steady component and the non-steady component included in the input signal. The steady component is a component having correlativity (periodicity). The non-steady component is a component having a lower correlativity (periodicity) than that of the steady component, and corresponds to, e.g., disturbance noise. However, there is a possibility that the non-steady component also includes useful information; therefore, it is undesirable to unreservedly remove the non-steady component. Therefore, the synthesis unit synthesizes the steady component and the non-steady component at a given ratio and outputs a synthesized signal.

The evaluation unit evaluates the magnitude of the amount of the non-steady component included in the input signal, and the synthesis unit modifies the given ratio (synthesis ratio between the steady component and the non-steady component) on the basis of the result of the evaluation. The first ratio is used in an instance in which the non-steady component is equal to or less than the predetermined reference, and the second ratio, in which the proportion of the non-steady component is smaller than that in the first ratio, is used in an instance in which the non-steady component exceeds the predetermined reference.

When the magnitude of the amount of the non-steady component exceeds the predetermined reference, the proportion of the non-steady component in the synthesis process thereby decreases, and the amount of the non-steady component is suppressed. Therefore, e.g., when sporadic disturbance noise exceeds the predetermined reference, the disturbance noise (signal to be removed), which is a non-steady component, is suppressed, and the steady component (signal that is required) is thereby highlighted to a greater extent. It is therefore possible to enhance the filter performance while reducing the processing load on the filter device. (2) According to a second aspect of the filter device of the invention, the synthesis unit has: a first amplifier that amplifies the steady component by a first gain; a second amplifier that amplifies the non-steady component by a second gain; and an adder that adds an output of the first amplifier and an output of the second amplifier; wherein taking as a first value the value of the first gain when the given ratio is the first ratio, and taking as a second value the value of the first gain when the given ratio is the second ratio, the filter device sets the second gain to zero, and uses a value greater than the first value as the second value of the first gain, in an instance in which the given ratio is the second ratio.

In the aspect described above, the steady component is amplified by the first gain and the non-steady component is amplified by the second gain. The value of the first gain can be equal to the first value, corresponding to an instance in which the first ratio is used, or the second value, corresponding to an instance in which the second ratio is used.

In the aspect described above, the second gain is set to zero, and a value greater than the first value is used as the second value of the first gain.

For example, in the first ratio, if the ratio between the steady component and the non-steady component is 1:0.5, the first value of the first gain is 1 and the second gain is 0.5. In the second ratio, if the ratio between the steady component and the non-steady component is 1.2:0, the second value of the first gain is 1.2 and the second gain is 0.

It is thereby possible, e.g., when sporadic disturbance noise exceeds the predetermined reference, to suppress the disturbance noise, which is a non-steady component, to a greater extent, and to highlight the steady component to a greater extent.

(3) According to a third aspect of the filter device of the invention, when the given ratio is set to the second ratio, the adaptive filter discontinues updating of the filter coefficient.

The filter coefficient is thereby prevented from being updated so as to track the non-steady component. Therefore, a decrease in the filter performance of the adaptive filter (performance in terms of separating the steady component and the non-steady component) is suppressed.

(4) According to a fourth aspect of the filter device of the invention, if a state in which the amount of the non-steady component is equal to or less than the predetermined reference is maintained over a first period, which lasts until a predetermined time has elapsed from a point in time at which the evaluation unit determines the amount of the non-steady component exceeds the predetermined reference, the filter device returns the given ratio from the second ratio to the first ratio at a point in time at which the first period has elapsed or after the first period has elapsed.

According to the aspect described above, if, after the synthesis ratio (given ratio) is switched from the first ratio to the second ratio, a state in which the amount of the non-steady component is equal to or less than the predetermined reference is maintained over the first period, which lasts until a predetermined time has elapsed from a point in time at which the switch has been made, the synthesis ratio is returned from the second ratio to the first ratio at the point in time at which the first period has elapsed or after the first period has elapsed.

In an instance in which, e.g., an excessively large disturbance noise momentarily enters the input signal and yet no excessively large disturbance noise subsequently enters the signal over the first period, it is thereby possible to again increase the synthesis ratio of the non-steady component, and perform a filtering process in a manner that makes more use of useful information included in the non-steady component.

(5) According to a fifth aspect of the filter device of the invention, if a state in which the amount of the non-steady component is equal to or less than the predetermined reference is maintained over a first period, which lasts until a predetermined time has elapsed from a point in time at which the evaluation unit determines the amount of the non-steady component exceeds the predetermined reference, the adaptive filter restarts the updating of the filter coefficient at the point in time at which the first period has elapsed or after the first period has elapsed.

According to the aspect described above, if, after the updating of the filter coefficient in the adaptive filter is discontinued, a state in which the amount of the non-steady component is equal to or less than the predetermined reference is maintained over the first period, which lasts until a predetermined time has elapsed from a point in time at which the updating has been discontinued (i.e., a point in time at which the synthesis ratio has been switched from the first ratio to the second ratio), the updating of the filter coefficient is restarted at the point in time at which the first period has elapsed or after the first period has elapsed.

In an instance in which, e.g., an excessively large disturbance noise momentarily enters the input signal and yet no excessively large disturbance noise subsequently enters the signal over the first period, it is thereby possible to again increase the synthesis ratio of the non-steady component, and perform a filtering process in a manner that makes more use of useful information included in the non-steady component.

(6) According to a sixth aspect of the filter device of the invention, in the second ratio, the proportion of the non-steady component is zero.

In the aspect described above, in the second ratio, the proportion of the non-steady component is set to zero. For example, if the ratio between the steady component and the non-steady component in the first ratio is 1:0.5, the ratio between the steady component and the non-steady component in the second ratio is 1:0. It is thereby possible, e.g., if sporadic disturbance noise increases beyond the predetermined reference, for the disturbance noise, which is a non-steady component, to be suppressed to a greater extent.

(7) According to a seventh aspect of the filter device of the invention, the input signal is a pulse wave signal including, as the steady components, a pulsation signal and a body motion component originating from body motion of a test subject; and, as the non-steady component, disturbance noise.

According to the aspect described above, the filter device is used to separate the pulsation signal and the body motion component originating from body motion of a test subject, included as the steady components in the pulse wave signal; from disturbance noise, included as the non-steady component in the pulse wave signal. The filter device has a high filter performance (performance in terms of separating the steady component and the non-steady component), and is therefore able to distinguish the pulsation signal from disturbance noise, and to highlight the pulsation to a greater extent.

(8) According to another aspect of the filter device of the invention, the filter device has a body motion filter that suppresses the body motion component.

The body motion component included in the post-filter signal outputted from the filter device is thereby suppressed (e.g., minimized). Applying the filter device to, e.g., a pulsation detection device for detecting a pulsation signal makes it possible for the pulsation signal to be more readily detected by the pulsation detection device.

BRIEF DESCRIPTION OF THE DRAWINGS

Referring now to the attached drawings which form a part of this original disclosure:

FIGS. 6A through 6C show a third example of measurement by the pulsation detection device.

DETAILED DESCRIPTION OF EXEMPLARY EMBODIMENTS

A description of the present embodiment shall now be given. The present embodiment described below is not intended to unduly limit the scope of the invention described in the claims. Furthermore, it is not necessarily the case that all of the configurations described in the present embodiment are essential constituent features of the invention.

A description will be given for an example in which a filter device according to the invention is applied to a pulsation detection device for detecting the pulsation signal in relation to a test subject. However, this example is not provided by way of limitation; the filter device according to the invention can be applied to a variety of other devices and instruments.

First Embodiment (Example of Overall Configuration)

Figure 1:
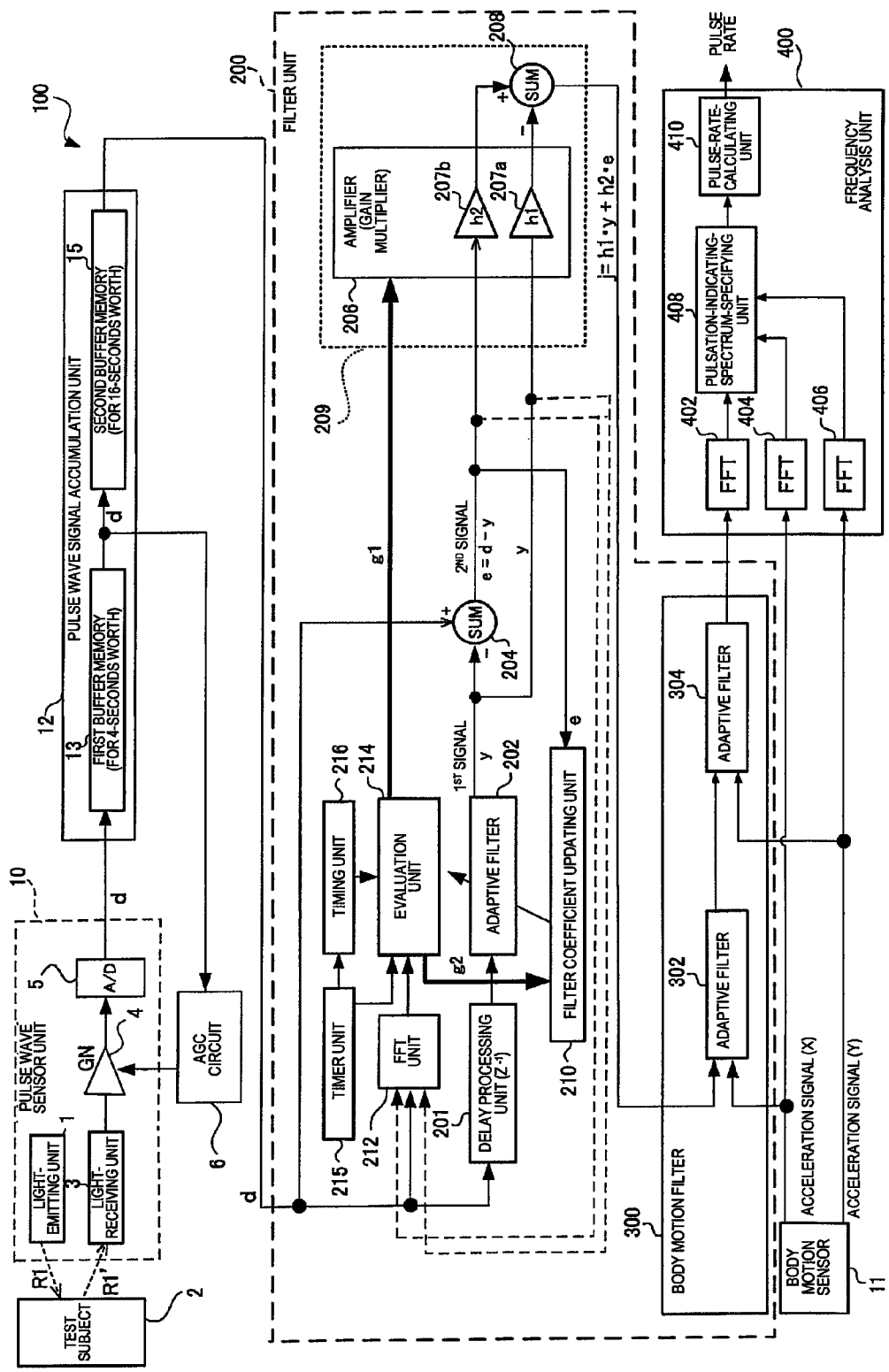
FIG. 1 shows the configuration of an example of a pulsation detection device including a filter device.

FIG. 1 shows the configuration of an example of a pulsation detection device including a filter device. The pulsation detection device 100 shown in FIG. 1 is a type of sensor device for detecting a pulsation signal originating from pulsation in a test subject (including people and animals).

In medical terms, pulsation refers to a movement that occurs when the heart or any other internal organ periodically contracts and relaxes in a repeated manner. Here, the movement of the heart acting as a pump for periodically pumping blood is referred to specifically as "pulsation." "Heart rate" refers to the number of pulsations of the heart per minute. "Pulse rate" refers to the number of pulsing movements in peripheral vessels. When the heart pumps out blood, a pulsing movement occurs in the arteries. A count of the pulsing movement is referred to as the "pulse rate" or, simply, the "pulse." As long as the pulse is measured on the arm, the term "pulse rate" is normally used in medicine instead of "heart rate." Also, in the following descriptions, the term "body motion" is used. In a broad sense, "body motion" refers to all movement of the body. Steady (periodic) body motion can be said to be body motion in a narrow sense. For example, steady and periodic movement of the arm (near the portion at which a pulse rate monitor is being worn) accompanying walking, jogging, or a similar activity is body motion in the narrow sense.

The pulsation detection device 100 shown in FIG. 1 has: an AGC circuit 6; a pulse wave sensor unit 10; a pulse wave signal accumulation unit (having a first buffer memory 13 for accumulating data for 4 seconds worth of a pulse wave signal d, and a second buffer memory 15 for accumulating data for 16 seconds worth of the pulse wave signal d) 12; a filter unit (preprocessing unit) 200, functioning as a filter device, provided with an adaptive filter 202 and a body motion filter 300; and a frequency analysis unit (post-processing unit) 400.

The pulse wave sensor unit 10 is, e.g., a photoelectric pulse wave sensor and a pulse wave sensor based on the principle thereof. The pulse wave sensor unit 10 has a light-emitting unit 1; a light-receiving unit 3 for receiving reflected light R1' generated by light R1 outputted from the light-emitting unit 1 being reflected by a blood vessel (biological information source) of a test subject 2, and converting the reflected light R1' into an electrical signal; a variable gain amplifier 4; and an A/D converter 5, which functions as a sampling unit. The gain GN of the variable gain amplifier 4 is automatically adjusted by the AGC circuit 6.

The pulse wave sensor unit 10 outputs a pulse wave signal d including a mixture of a pulsation signal, a body motion signal originating from body motion of the test subject (person or animal), and a disturbance noise signal. Specifically, the pulse wave signal d includes, e.g., a pulsation signal and a body motion signal, which are steady components (components having correlativity or periodicity); and disturbance noise (sporadic noise, etc.), which is a non-steady component (a component having lower correlativity or periodicity than steady components).

A signal corresponding to 4 seconds worth of the pulse wave signal d outputted from the pulse wave sensor unit 10 is accumulated in the first buffer memory 13. 4 seconds worth of the pulse wave signal d is transferred to the second buffer memory 15 in 4-second cycles. The second buffer memory 15 is a first-in, first-out (FIFO) memory, and 16 seconds worth of the pulse wave signal is updated in 4-second units. 16 seconds worth of the pulse wave signal is accumulated because it is necessary, when frequency analysis is used to specify the pulsation component, to observe the fluctuation in the signal for a time width of a certain size and carefully examine, e.g., whether or not a correlation exists.

The filter unit 200 functioning as a filter device has: a delay processing unit 201 for delaying an input signal (pulse wave signal d in this instance) by one sampling time; an adaptive filter 202; a subtractor 204; a synthesis unit 209 including an amplifier (gain multiplier) 206 and an adder 208; a filter coefficient updating unit 210 for updating the filter coefficient of the adaptive filter 202; an FTF unit 212; an evaluation unit 214 for evaluating the magnitude of the amount of a non-steady component included in the input signal (pulse wave signal d); a timer unit 215 for outputting time information; a timing unit 216 for generating a timing signal based on the time information; and a body motion filter 300.

The amplifier (gain multiplier) 206 has a first amplifier 207a and a second amplifier 207b. The gain of the first amplifier 207a is referred to as a first gain $h1$ and the gain of the second amplifier 207b is referred to as a second gain $h2$.

The adaptive filter 202 is a filter for separating a steady component and a non-steady component included in the input signal (pulse wave signal d), and is a filter in which updating of a filter coefficient causes frequency response characteristics to adapt in an autonomous fashion.

A steady component having high autocorrelation is defined as a first signal y; and a non-steady component obtained by subtracting the first signal y from the pulse wave signal d, the non-steady component having lower autocorrelation than the first signal y, is defined as a second signal $e$ (=d−y). The subtractor 204 generates the second signal $e$ (=d−y).

The first amplifier (first gain multiplier) 207a multiplies the first signal by the first gain $h1$. The second amplifier (second gain multiplier) 207b multiplies the second signal e with the second gain $h2$. At a point in time at which the pulsation detection device 100 starts measurement, $h1$ is set so that $h1 \geq 1.0$, and $h2$ is set so that $h2<1.0$. It is thereby possible to mitigate any effect of an impact, and increase the capability of tracking sudden changes in the pulsation signal or the body motion signal.

The first signal y, after being multiplied by the first gain $h1$; and the second signal e, after being multiplied by the second gain $h2$, are added (synthesized) by the adder 208. The synthesis generates a post-filter signal $j$ (=$h1 \cdot y + h2 \cdot e$). The post-filter signal j is supplied to the body motion filter 300.

The second signal $e$ (=d−y), which is a non-steady component, is a component having a lower correlativity (periodicity) than that of the first signal y, which is a steady component, and corresponds to, e.g., disturbance noise. However, there is a possibility that the second signal e, which is a non-steady component, also includes useful information; therefore, it is not preferable to unreservedly remove the second signal e. For example, when the exercise state of the test subject 2 is undergoing a change, the second signal e includes a signal component representing the change in exercise state. Therefore, a second signal e having a certain size is necessary for the adaptive filter 202 to track the change in exercise state of the test subject 2. Therefore, the synthesis unit 209 synthesizes, at a given ratio, the first signal y, which is a steady component included in the input signal (pulse wave signal d), and the second signal e (=d−y), which is a non-steady component; and outputs a synthesized signal.

The given ratio (synthesis ratio) is determined by the ratio between the first gain h1 and the second gain h2. The given ratio (synthesis ratio) is modified in accordance with a result of an evaluation of the pulse wave signal d performed by the evaluation unit 214 (this will be described further below).

The filter coefficient updating unit 210 updates, in an adaptive manner, the filter coefficient (a normalized least mean square (nLMS) coefficient in this instance) of the adaptive filter 202 so that the value of the second signal e is suppressed (e.g., minimized). The process of updating the filter coefficient of the adaptive filter 202 is discontinued on the basis of the result of the evaluation of the pulse wave signal d performed by the evaluation unit 214 (this will be described further below).

A function block including the delay processing unit 201, the adaptive filter 202, and the filter coefficient updating unit 210 may be referred to as an adaptive line enhancer.

The FFT unit 212 performs a fast Fourier transform (FFT) process on at least one of the pulse wave signal d inputted into the filter unit 200; the first signal y, which is the separated steady component; and the second signal e (=d−y), which is the separated non-steady component; and generates a frequency spectrum.

The evaluation unit 214 evaluates, on the basis of the frequency spectrum generated by the FFT unit 212 (i.e., a frequency analysis result), the magnitude of the amount of the non-steady component included in the input signal d. The filter unit 200, functioning as the filter device, sets the given ratio in the synthesis unit 209 to a first ratio in an instance in which the evaluation unit 214 determines the amount of the non-steady component to be equal to or less than a predetermined reference, and sets the given ratio to a second ratio, in which the proportion of the non-steady component is less than that of the first ratio, in an instance in which the evaluation unit 214 determines the amount of the non-steady component to exceed the predetermined reference.

In other words, the first ratio is used in an instance in which the non-steady component is equal to or less than the predetermined reference; and the second ratio, in which the proportion of the non-steady component is less than that of the first ratio, in an instance in which the amount of non-steady component exceeds the predetermined reference. An example of a method for determining whether or not the non-steady component is equal to or less than the predetermined reference is a method in which a determining process, in which a predetermined evaluation indicator is used, is performed on the basis of a frequency spectrum of the pulse wave signal d, and the degree of cleanness of the pulse wave signal d (measure of disturbance noise present) is determined (described further below).

The proportion of the non-steady component in the synthesis process is thereby lowered when the magnitude of the amount of the non-steady component exceeds the predetermined reference, and the amount of non-steady component is minimized. Therefore, e.g., when sporadic disturbance noise increases beyond the predetermined reference, the disturbance noise (the second signal e to be removed), which is a non-steady component, is suppressed, and the steady component (the first signal y, which is required), is thereby highlighted to a greater extent.

According to this configuration, there is no need to provide a plurality of band pass filters. It is thereby possible to enhance the filter performance while reducing the processing load on the filter device. A variety of modifications or applications are possible with regards to the method for controlling the operation of the filter unit 200 on the basis of the result of the evaluation performed by the evaluation unit 214. These will be described together further below as examples of operation of the filter unit.

In FIG. 1, a body motion sensor 11 is a sensor for detecting the body motion (body motion in a broad sense) of the test subject 2. The body motion (in the broad sense) includes body motion in the narrow sense, such as, e.g., steady or periodic movement of the arm (near a portion at which a pulse rate monitor is being worn) accompanying walking, jogging, and other activity. The body motion sensor 11 can include, e.g., an acceleration sensor or a gyro sensor.

The body motion filter 300 has a first adaptive filter 302 and a second adaptive filter 304 for removing the body motion signal. The body motion signal (body motion noise) is a signal, contained in the pulse wave signal (or more accurately, the post-filter signal j outputted from the adder 208), representing the change in vascular volume caused by a movement or an action performed by a person or an animal (body motion). For example, in an instance of a pulse rate monitor worn on the arm or the finger, the arm-swinging motion during walking or jogging has an effect of causing a change in vascular volume in synchronization with the rhythm of the arm-swinging motion. A steady motion performed by a person generates a body motion signal component (a component corresponding to a body motion signal in the narrow sense) corresponding to the steady body motion. The body motion signal component in this instance is known to highly correlate with the waveform of a signal outputted by the body motion sensor 11 worn near the portion at which the pulse wave sensor unit 10 is worn.

The frequency analysis unit (postprocessing unit) 400 has an FFT unit 402, into which is inputted a signal from which the body motion signal has been removed; an FFT unit 404, into which an acceleration signal (x-axis-direction component) from the body motion sensor 11 is inputted; an FFT unit 406, into which an acceleration signal (y-axis-direction component) from the body motion sensor 11 is inputted; a pulsation-indicating-spectrum-specifying unit 408; and a pulse-rate-calculating unit 410.

The pulsation-indicating-spectrum-specifying unit 408 performs a frequency analysis every 4 seconds on 16 seconds worth of the pulse wave signal after being subjected to FFT; examines, on the basis of variables such as the spectral value or the spectral distribution, the correlativity with respect to a pulsation component obtained in the past, or another parameter; and specifies a pulsation-indicating spectrum.

The pulsation-indicating spectrum is a frequency spectrum, as part of a frequency spectrum obtained as a result of performing FFT on the pulsation component signal for a set period, that shows the period and the signal strength of the pulsation. The body-motion-indicating spectrum is a frequency spectrum, as part of a spectrum obtained as a result of performing FFT on the body motion component signal for a set period, that shows the period and the signal strength of the body motion (e.g., arm-swinging during walking).

The pulse-rate-calculating unit 410 calculates the pulse rate. When the position (frequency) of the pulsation-indicating spectrum on a frequency axis has been established, the pulse rate is unambiguously established so as to correspond with the position of the spectrum. The calculated pulse rate can be displayed, e.g., on a display unit (not shown). A waveform representing the pulsation, calories consumed by the test subject 2, the current time, and other information can also be displayed alongside.

Thus, in the example shown in FIG. 1, the filter unit 200 functioning as the filter device is used to separate the pulsation signal and the body motion signal originating from the body motion of the test subject, which are steady components; and disturbance noise, which is a non-steady component, included in the pulse wave signal d. The filter unit 200 functioning as the filter device has a high filter performance (performance in terms of separating the steady components and the non-steady component), and is therefore capable of distinguishing the pulsation signal from disturbance noise, and of highlighting the pulsation signal to a greater extent.

In the example shown in FIG. 1, the filter unit 200 functioning as the filter device has the body motion filter 300 for suppressing the body motion component. The body motion component included in the post-filter signal j outputted from the filter unit 200 is suppressed. Therefore, the pulsation signal can be more readily detected by the frequency analysis unit 400.

(Example of Operation of Filter Unit)

As described above, a variety of modifications or applications are possible with regards to the method for controlling the operation of the filter unit 200 on the basis of the evaluation performed by the evaluation unit 214. A specific description will now be given.

First, a description will be given for a specific example of operation of the evaluation unit 214. As described above, the evaluation unit 214 determines whether or not the non-steady component included in the pulse wave signal d, which is a signal inputted into the filter unit 200, is equal to or less than a predetermined reference.

An example of a method for the determining is a method in which a determining process, in which a predetermined evaluation indicator is used, is performed on the basis of a frequency spectrum (generated by the FFT unit 212) of the pulse wave signal d, and the degree of cleanness of the pulse wave signal d (measure of disturbance noise present) is determined.

Figure 2:
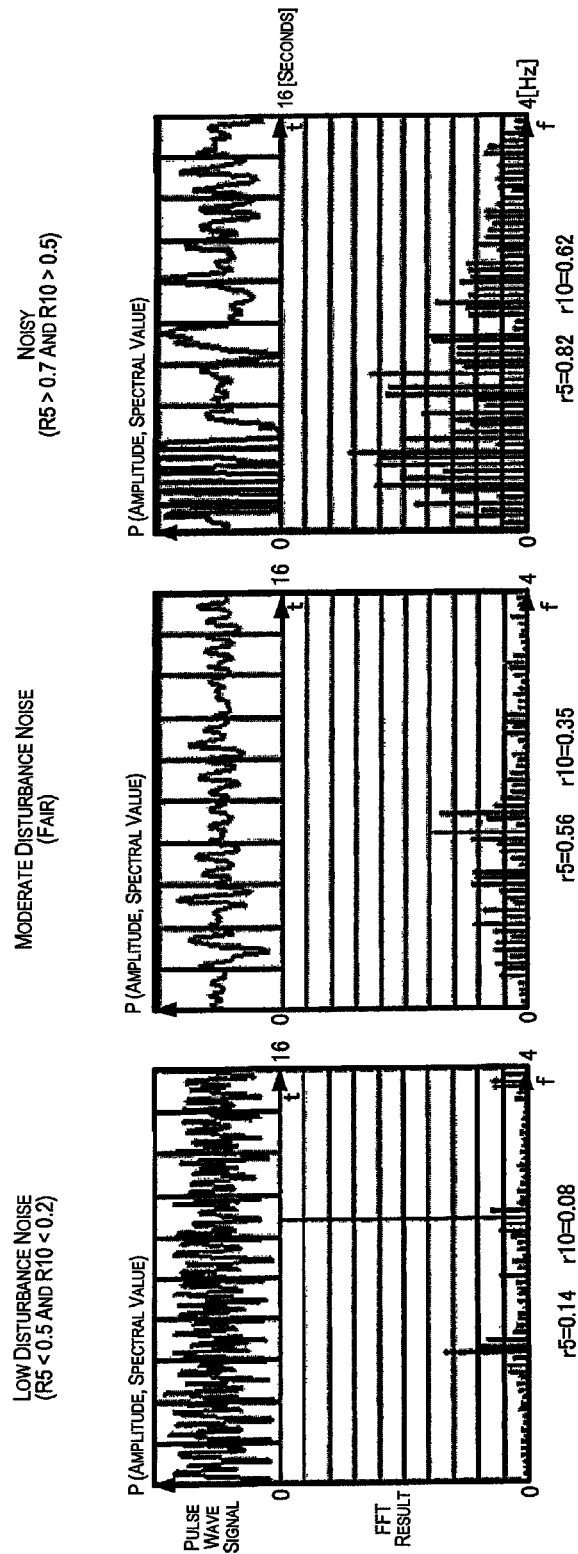
FIGS. 2A through 2C are used to illustrate a method for using a predetermined evaluation indicator to determine the degree of cleanness (the magnitude of the amount of disturbance noise) of the pulse wave signal.

FIGS. 2A through 2C are used to illustrate a method for using a predetermined evaluation indicator to determine the degree of cleanness (measure of the amount of disturbance noise) of the pulse wave signal. In each of FIGS. 2A through 2C, the upper side shows a signal waveform of the pre-FFT pulse wave signal d corresponding to 16 seconds. The horizontal axis represents time and the vertical axis represents the amplitude of the signal. The lower side shows the frequency spectrum in a frequency region from 0 to 4 Hz. The horizontal axis represents the frequency and the vertical axis represents the spectral value.

FIG. 2A shows the waveform and the frequency spectrum of the pulse wave signal d in an instance in which there is low disturbance noise (i.e., the signal is clean). FIG. 2B shows the waveform and the frequency spectrum of the pulse wave signal in an instance in which there is moderate disturbance noise (i.e., the signal is fair). FIG. 2C shows the waveform and the frequency spectrum of the pulse wave signal d in an instance in which the pulse wave signal d includes a high level of disturbance noise (i.e., the signal is noisy). As can be seen from comparing FIGS. 2A through 2C, the waveform and the frequency spectrum of the pulse wave signal d are closely related. The state of distribution and the spectral value of the frequency spectrum change in accordance with the waveform of the pulse wave signal.

Therefore, the evaluation unit 214 is capable of evaluating (estimating), on the basis of the frequency spectrum generated by the ITT unit 212, the state of disturbance noise superimposed on the pulse wave signal d, i.e., the magnitude of the amount of disturbance noise, which is a non-steady component, In the present embodiment, a ratio of key spectral values in the frequency spectrum (i.e., ratio of baseline heights) are used as an indicator for evaluating the magnitude of the amount of disturbance noise (the magnitude of the amount of the non-steady component). Specifically, indicators $r_5$ and $r_{10}$ are used (this is only an example, and another statistical indicator, such as standard deviation, can be used).

$r_5$ is an indicator obtained by arranging (i.e., sorting) five spectra, in descending order of the peak value, from a frequency spectrum of 16-seconds worth of the pulse wave signal, and taking a spectral value (power) of the first spectrum as the denominator and a spectral value (power) of the fifth spectrum as the numerator.

$r_{10}$ is an indicator obtained by arranging (i.e., sorting) ten spectra in the sequence of the size of the peak value from a frequency spectrum of 16-seconds worth of the pulse wave signal, and taking a spectral value (power) of the first spectrum as the denominator and a spectral value (power) of the tenth spectrum as the numerator.

Here, as an example, an instance in which $r_5<0.5$ and $r_{10}<0.2$ is defined to have low noise (clean), an instance in which $r_5>0.7$ and $r_{10}>0.5$ is defined to have high noise (noisy), and an instance in which neither of the above apply is defined to have moderate noise (fair).

In the example shown in FIG. 2A, since $r_5=0.14$ and $r_{10}=0.08$, the noise is determined to be low (clean). In the example shown in FIG. 2B, since $r_5=0.56$ and $r_{10}=0.35$, the noise is determined to be moderate (fair). In the example shown in FIG. 2C, since $r_5=0.82$ and $r_{10}=0.62$, the noise is determined to be high (noisy).

Whether the non-steady component included in the pulse wave signal d is exceeding the predetermined reference, or is equal to or less than the reference, can be determined from, e.g., whether or not the degree of cleanness of the pulse wave signal d corresponds to "noisy" (state shown in FIG. 2C). In other words, when the signal is noisy, the evaluation unit 214 determines the non-steady component included in the pulse wave signal d to be exceeding the predetermined reference, and when the signal is not noisy (i.e., clean or fair), the evaluation unit 214 determines the non-steady component included in the pulse wave signal d to be equal to or less than the predetermined reference. Such a determining process is performed by the evaluation unit 214 shown in FIG. 1.

Upon evaluating the magnitude of the amount of the non-steady component in the input signal (pulse wave signal d), the evaluation unit 214 outputs a signal g1 indicating the result of the evaluation. The value of each of the first gain h1 and the second gain h2 in the amplifier (gain multiplier 206) is determined on the basis of the signal g1.

The synthesis ratio (the given ratio described above) in the synthesis unit 209 is determined by the first gain h1 and the second gain h2. Therefore, the filter device 200 modifies the given ratio (synthesis ratio between the steady component and the non-steady component) on the basis of the result of the evaluation performed by the evaluation unit 214.

As described above, in an instance in which the non-steady component included in the pulse wave signal d is equal to or less than the predetermined reference (i.e., in an instance in which the degree of cleanness of the signal does not correspond to "noisy"), the first ratio is used as the synthesis ratio (given ratio); and in an instance in which the non-steady component exceeds the predetermined reference (i.e., in an instance in which the signal is "noisy"), the second ratio, in which the proportion of the non-steady component is smaller than that of the first ratio, is used.

For example, in the first ratio, the ratio between the steady component and the non-steady component (ratio between the first gain h1 and the second gain h2) can be 1:0.5, and in the second ratio, the ratio between the steady component and the non-steady component (ratio between the h1 and h2) can be 1:0.2.

When the magnitude of the amount of the non-steady component exceeds the predetermined reference, the proportion of the non-steady component in the synthesis process in the synthesis unit 209 thereby decreases, and the amount of the non-steady component is suppressed. Therefore, e.g., if sporadic disturbance noise increases beyond the predetermined reference, the disturbance noise (the second signal e to be removed), which is a non-steady component, is suppressed, and the steady component (the first signal y, which is required), is thereby highlighted to a greater extent. According to this configuration, there is no need to provide a plurality of band pass filters. It is thereby possible to enhance the filter performance while reducing the processing load on the filter device.

In an instance in which the second ratio is used, the proportion of the non-steady component can also be zero. For example, when the ratio between the steady component and the non-steady component (ratio between h1 and h2) in the first ratio is 1:0.5, the ratio between the steady component and the non-steady component in the second ratio can be 1:0. It is thereby possible, e.g., if sporadic disturbance noise increases beyond the predetermined reference, for the disturbance noise, which is a non-steady component, to be suppressed to a greater extent.

The value of the first gain h1 when the first ratio is used (i.e., a first value) and the value of the first gain h1 when the second ratio is used (i.e., a second value) can be different from each other.

For example, taking as a first value the value of the first gain h1 when the synthesis ratio (given ratio) is the first ratio, and taking as a second value the value of the first gain h1 when the synthesis ratio (given ratio) is the second ratio, the filter unit 200 functioning as the filter device can set the second gain h2 to zero, and use a value greater than the first value as the second value of the first gain h1, in an instance in which the synthesis ratio (given ratio) is the second ratio.

For example, if the ratio between the steady component and the non-steady component in the first ratio is 1:0.5, the first value of the first gain h1 is 1, and the second gain h2 is 0.5. If the ratio between the steady component and the non-steady component is 1.2:0, the second value of the first gain h1 is 1.2, and the second gain h2 is 0.

It is thereby possible, e.g., when sporadic disturbance noise increases beyond the predetermined reference, to suppress the disturbance noise to a greater extent, and highlight the steady component to a greater extent.

When the second ratio is used as the synthesis ratio (given ratio) on the basis of the result of the evaluation performed by the evaluation unit 214, the adaptive filter 202 can discontinue the updating of the filter coefficient. In the example shown in FIG. 1, in an instance in which the evaluation unit 214 makes an evaluation that the magnitude of the amount of the non-steady component exceeds the predetermined reference, the evaluation unit 214 outputs a signal g2 to the filter coefficient updating unit 210. Upon receiving the signal g2, the filter coefficient updating unit 210 discontinues the updating of the filter coefficient.

The filter coefficient is thereby prevented from being updated so as to track the non-steady component. A decrease in the filter performance (performance in terms of separating the steady component and the non-steady component) of the adaptive filter 202 is thereby suppressed.

If a state in which the amount of the non-steady component is equal to or less than the predetermined reference is maintained over a first period, which lasts until a predetermined time has elapsed from a point in time at which the evaluation unit 214 determines the amount of the non-steady component exceeds the predetermined reference, the filter device 200 can return the synthesis ratio (given ratio) from the second ratio to the first ratio at a point in time at which the first period has elapsed or after the first period has elapsed. For example, by changing the level of the signal g1 outputted from the evaluation unit 214, it is possible to modify the synthesis ratio (given ratio) in the synthesis unit 209 from the second ratio to the first ratio.

In an instance in which, e.g., an excessively large disturbance noise momentarily enters the input signal (pulse wave signal d) and yet no excessively large disturbance noise subsequently enters the signal over the first period, it is thereby possible to again increase the synthesis ratio (given ratio) of the non-steady component, and, e.g., to perform a filtering process in a manner that makes more use of useful information included in the non-steady component.

Also, if a state in which the amount of the non-steady component is equal to or less than the predetermined reference is maintained over the first period, which lasts until a predetermined time has elapsed from a point in time at which the evaluation unit 214 determines the amount of the non-steady component exceeds the predetermined reference, the filter device 200 can restart the updating of the filter coefficient, which had been discontinued, at the point in time at which the first period has elapsed or after the first period has elapsed. For example, by changing the level of the signal g2 outputted from the evaluation unit 214, it is possible to restart the updating of the filter coefficient.

In an instance in which, e.g., an excessively large disturbance noise momentarily enters the input signal (pulse wave signal d) and yet no excessively large disturbance noise subsequently enters the signal over the first period, it is thereby possible to restart the updating of the filter coefficient, and, e.g., to perform a filtering process in a manner that makes use of useful information included in the non-steady component.
(Process Flow of Pulsation Detection Device)

Figure 3:
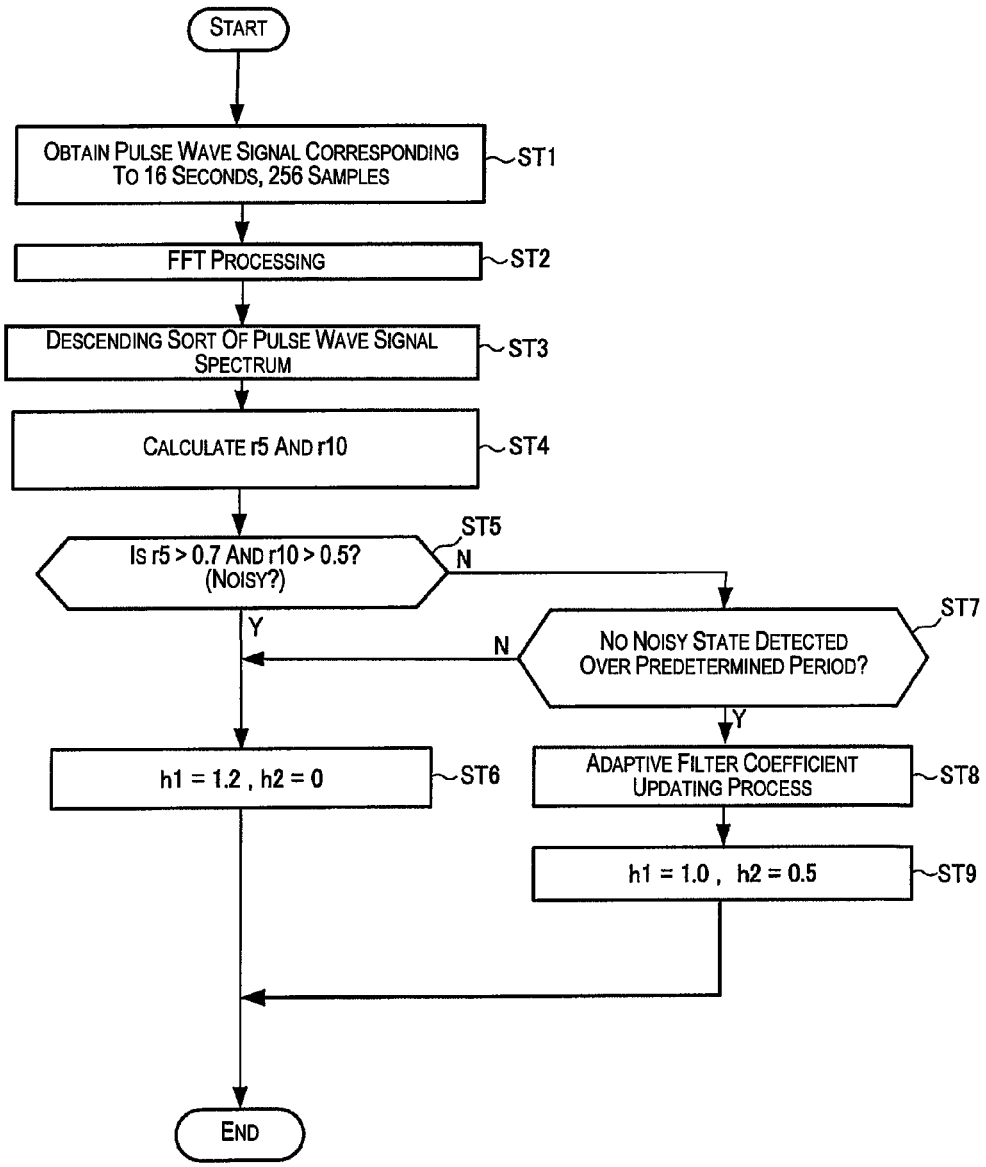
FIG. 3 is a flow chart showing an example of the operation procedure for the pulsation detection device.

FIG. 3 is a flow chart showing an example of the operation procedure for the pulsation detection device. First, the pulse wave signal corresponding to 256 samples over 16 seconds is obtained (step ST1). Next, a FFT process is performed by the FFT unit 212 (step ST2). The evaluation unit 214 performs a descending sort on the spectrum of the pulse wave signal d (step ST3). Next, evaluation indicators r5 and r10 are calculated (step ST4).

Next, the evaluation unit 214 determines whether r5>0.7 and r10>0.5, i.e., whether or not the pulse wave signal d is in a high noise (noisy) state (step ST5).

In an instance in which the result of step ST5 is "Yes", the first gain h1 in the synthesis unit 209 becomes 1.2 and the second gain h2 becomes 0 (step ST6). A step corresponding to a process of updating the adaptive filter coefficient (i.e., a step corresponding to step ST8) does not exist between steps ST5 and ST6; therefore, in an instance in which step ST6 is performed, the updating of the adaptive filter coefficient by the adaptive filter coefficient updating unit 210 is discontinued. Also, in an instance in which the result of step ST5 is "No", a determination is made as to whether or not a state that is not noisy has been maintained over a predetermined period (i.e., the first period described further above) (step ST7).

If the result of step ST7 is "No", the flow proceeds to step ST6. If the result of step ST7 is "Yes", the process of updating the adaptive filter 202 is performed (step ST8), the first gain h1 in the synthesis unit 209 becomes 1.0, and the second gain h2 becomes 0.5 (step ST9).

A description will now be given for several measurement examples.

FIRST MEASUREMENT EXAMPLE

Figure 4A:
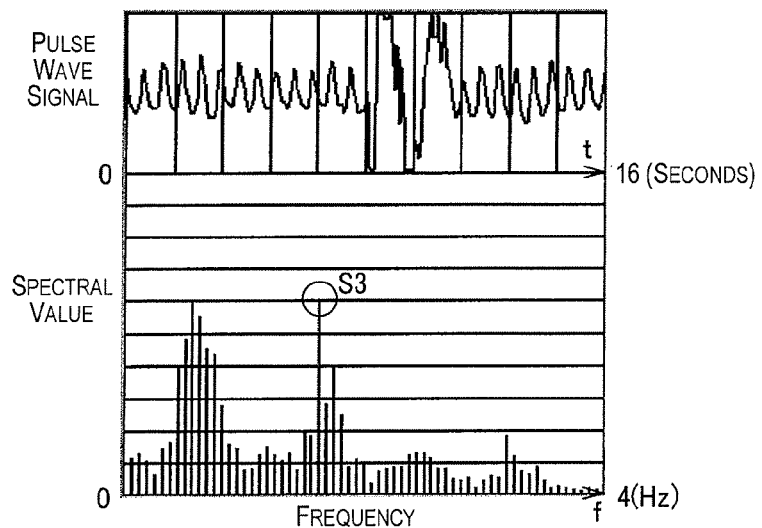
FIGS. 4A and 4B show a first example of measurement by the pulsation detection device.
Figure 4B:
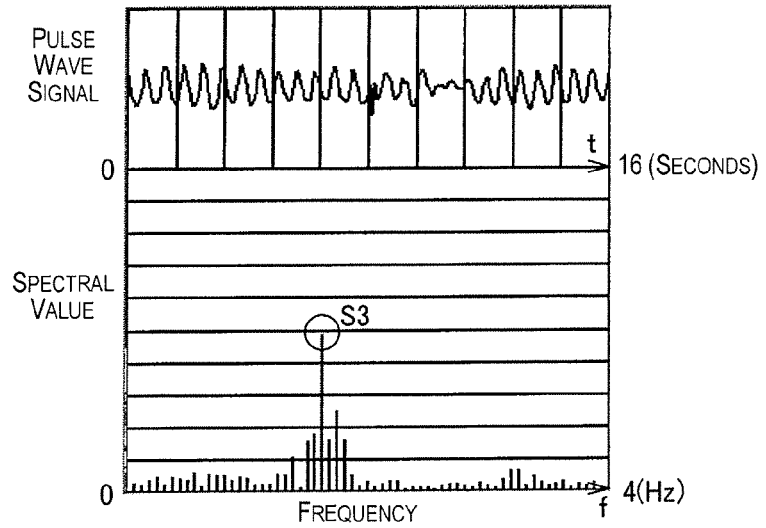

FIGS. 4A and 4B show a first example of measurement by the pulsation detection device. The first measurement example is an example of an instance in which sporadic disturbance noise has occurred when the test subject 2 was in a state of rest. FIG. 4A shows the frequency spectrum of the pulse wave signal d before being subjected to filtering by the filter unit 200, and FIG. 4B shows the frequency spectrum of a post-filtering signal j. In each of FIGS. 4A and 4B, the upper side shows the signal waveform of the pre-FFT pulse wave signal d corresponding to 16 seconds. The horizontal axis represents time t and the vertical axis represents the amplitude of the signal. The lower side shows the frequency spectrum in a frequency region from 0 to 4 Hz. The horizontal axis represents the frequency f and the vertical axis represents the spectral value.

Here, an indicator referred to as SN3 is used to objectively evaluate the filter performance of the filter unit 200. SN3 is an S/N indicator for evaluating the performance of the filter unit 200, and is an indicator obtained by dividing the total of the spectral value of the pulsation-indicating spectrum and each of a left and a right spectral value on either side of the pulsation-indicating spectrum on the frequency axis by a total value of the frequency spectra that appear in all frequency regions being observed. Specifically, SN3 can be represented using the following computation formula.

SN3=(total of pulsation-indicating spectrum and each spectral value on either side thereof)/(total of spectral values in all frequencies 0 to 4 Hz) (unit: %) The pulsation-indicating spectrum is a frequency spectrum, as part of a frequency spectrum obtained as a result of performing FFT on the pulsation component signal for a set period, that shows the period and the signal strength of the pulsation.

SN3 is used as an indicator because the extent of degradation in the performance of the filter unit 200 can be determined from the proportion, in relation to the total of all spectral values in the frequency region being observed, of the spectral value of a high-correlativity signal component (pulsation component) to be extracted.

In the first measurement example, the test subject 2 is in a state of rest, but has temporarily performed an irregular action, resulting in sporadic noise entering the pulse wave signal d. When the sporadic noise enters the signal, the signal is determined to be noisy in step ST5 in the flowchart shown in FIG. 3. Therefore, in step ST6, the first gain h1 in the synthesis unit 209 becomes 1.2 and the second gain h2 becomes 0.

As a result, disturbance noise, which is a non-steady component, is suppressed, and it is possible to highlight the steady component. Therefore, the pulsation-indicating-spectrum-specifying unit 408 can perform the process of specifying the pulsation-indicating spectrum on the basis of the post-filtering signal j having little disturbance noise. The accuracy of the process of specifying the pulsation-indicating spectrum is therefore enhanced.

During the period in which the sporadic noise is present, the filter coefficient updating unit 210 suspends the process of updating the adaptive filter coefficient. Therefore, the adaptive filter 202 does not track the disturbance noise, and as a result, the filter performance of the adaptive filter is prevented from decreasing.

As can be seen from a comparison between FIGS. 4A and 4B, it is clear that filtering performed by the filter unit 200 is reducing sporadic noise. Specifically, spectral values of spectra unrelated to the pulsation, in a low frequency region (around 0.3 Hz), have been clearly made smaller.

In the example shown in FIG. 4A, SN3 is 11.5%, and in the example shown in FIG. 4B, SN3 is 27.8%. SN3 has a larger value after filtering. The pulsation-indicating-spectrum-specifying unit 408 is thereby able to more readily specify the pulsation-indicating spectrum.

SECOND MEASUREMENT EXAMPLE

A second measurement example is an example of measuring the pulse when the test subject 2 is in a state of rest. This corresponds to a result of measurement in an instance in which, e.g., the test subject 2, having temporarily performed an irregular action while in a state of rest and subsequently completing the irregular action and returning to a state of rest, maintains the state of rest.

Figure 5A:
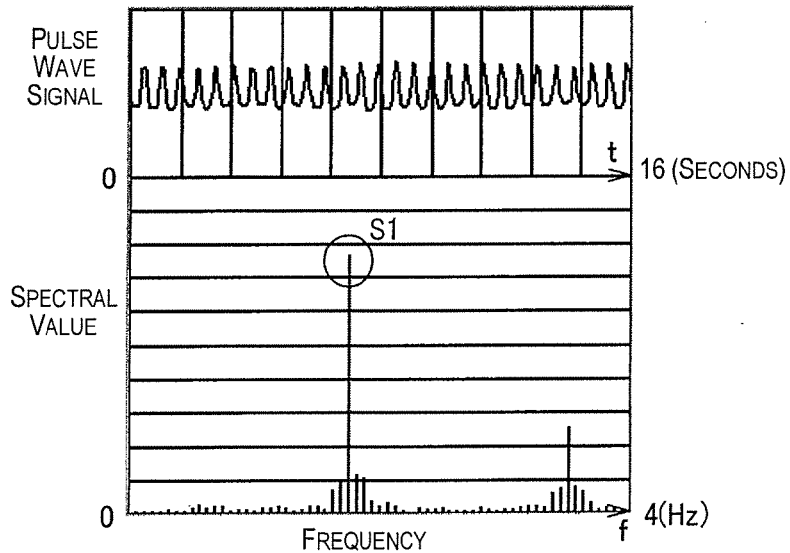
FIGS. 5A and 5B show a second example of measurement by the pulsation detection device.
Figure 5B:
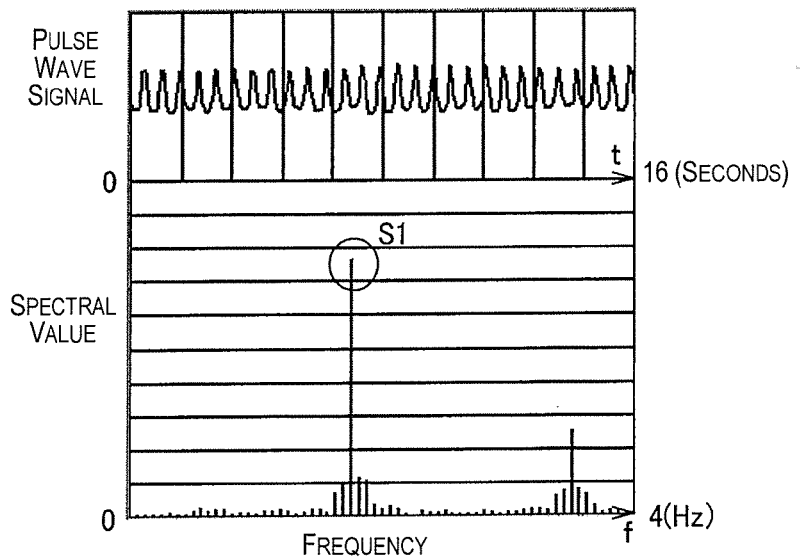

FIGS. 5A and 5B show the second example of measurement by the pulsation detection device. FIG. 5A shows the frequency spectrum of the pulse wave signal d before being subjected to filtering by the filter unit 200, and FIG. 5B shows the frequency spectrum of a post-filtering signal j. In each of FIGS. 5A and 5B, the upper side shows the signal waveform of the pre-FFT pulse wave signal d corresponding to 16 seconds. The horizontal axis represents time t and the vertical axis represents the amplitude of the signal. The lower side shows the frequency spectrum in a frequency region from 0 to 4 Hz. The horizontal axis represents the frequency f and the vertical axis represents the spectral value.

As described in the first measurement example, during the period in which sporadic disturbance noise is present, the process of updating the adaptive filter coefficient is suspended, and the filter performance of the adaptive filter is prevented from decreasing. This effect (i.e., the effect in which a decrease in filter performance due to sporadic noise that has occurred in the past is suppressed) enhances the accuracy of specifying the pulsation-indicating spectrum in the present measurement example, compared to an instance in which the process of updating the adaptive filter coefficient is not suspended.

In the example shown in FIG. 5A, SN3 is 42.5%. In contrast, in the example shown in FIG. 5B, SN3 is 48.9%. Filtering performed by the filter unit 200 is causing the value of SN3 (indicator value) to increase. Specifically, the pulsation-indicating spectrum (spectrum S1 circled in FIGS. 5A and 5B) is highlighted relative to other spectra representing other frequencies. The pulsation-indicating-spectrum-specifying unit 408 is thereby able to more readily specify the pulsation-indicating spectrum.

THIRD MEASUREMENT EXAMPLE

A third measurement example is an example of measurement of the pulse when the test subject 2 is walking. FIGS. 6A through 6C show the third example of measurement by the pulsation detection device. FIG. 6A shows the frequency spectrum of the pulse wave signal d before being subjected to filtering by the filter unit 200, FIG. 4B shows the frequency spectrum of a post-filtering signal j, and FIG. 6C shows the frequency spectrum of a signal after removal of the body motion component. In each of FIGS. 6A through 6C, the upper side shows the signal waveform of the pre-FFT pulse wave signal d corresponding to 16 seconds. The horizontal axis represents time t and the vertical axis represents the amplitude of the signal. The lower side shows the frequency spectrum in a frequency region from 0 to 4 Hz. The horizontal axis represents the frequency f and the vertical axis represents the spectral value.

When the test subject 2 is in a walking state, the possibility of sporadic noise entering the pulse wave signal d can be thought to be higher than that in an instance in which the test subject 2 is in a state of rest. As already described, when sporadic noise enters the signal, the signal is determined to be noisy in step ST5 in the flow chart shown in FIG. 3; therefore, in step ST6, the first gain hi in the synthesis unit 209 becomes 1.2 and the second gain h2 becomes 0. As a result, disturbance noise, which is a non-steady component, is suppressed, and it is possible to highlight the steady component. Therefore, the pulsation-indicating-spectrum-specifying unit 408 can perform the process of specifying the pulsation-indicating spectrum on the basis of the post-filtering signal j having little disturbance noise. The accuracy of the process of specifying the pulsation-indicating spectrum is therefore enhanced.

In an instance in which disturbance noise equal to or higher than a predetermined threshold value has been inputted, the updating of the filter coefficient is discontinued. A decrease in filter performance due to sporadic disturbance noise that has occurred in the past and sporadic disturbance noise that is occurring at the present time is thereby suppressed. Therefore, in the present measurement example, the accuracy of specifying the pulsation-indicating spectrum is again improved over an instance in which the process of updating the adaptive filter coefficient is not suspended.

In the third measurement example, the test subject 2 is walking. Therefore, the pulse wave signal d includes, in addition to the pulsation component, a body motion component originating from body motion. Therefore, the frequency spectrum includes a body-motion-indicating spectrum in addition to the pulsation-indicating spectrum.

In each of FIGS. 6A through 6C, the spectrum S2 indicated by a circle is the pulsation-indicating spectrum. SN3 in the example shown in FIG. 6A is 20.2%. SN3 in the example shown in FIG. 6B is 23.5%, and is higher than in the example shown in FIG. 6A. Specifically, the pulsation-indicating spectrum S2 is highlighted relative to other spectra representing other frequencies. In the example shown in FIG. 6C, SN3 has increased to 41.8%. Thus, the pulsation-indicating-spectrum-specifying unit 408 is able to more readily specify the pulsation-indicating spectrum.

Thus, according to the pulsation detection device of the present embodiment, disturbance noise, which is a non-steady component, is constrained in an effective manner; and the pulsation signal, which is a steady component, is further highlighted. The pulsation-indicating spectrum can thereby be more readily specified.

Figure 7A:
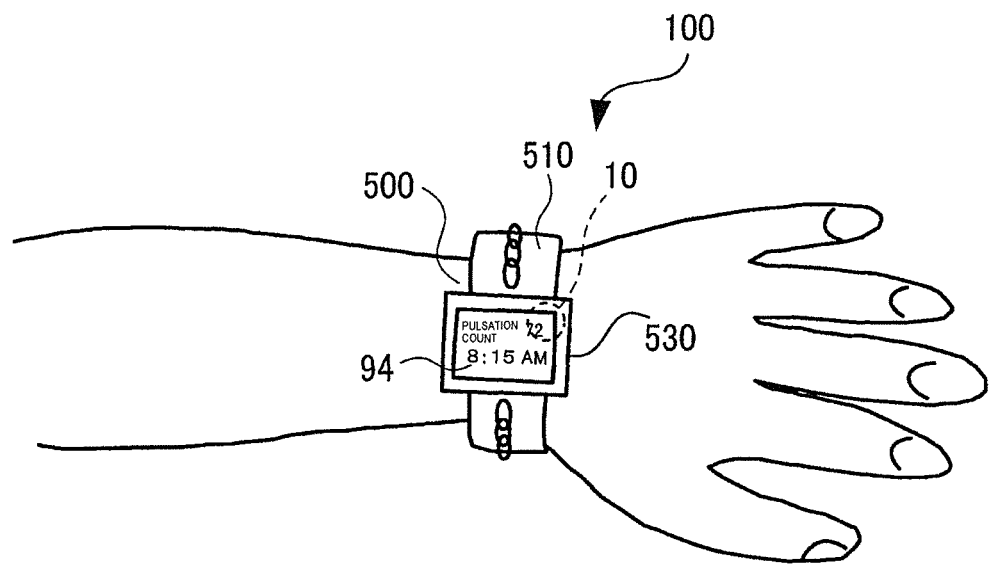
FIGS. 7A and 7B show examples in which the pulsation detection device is worn by the test subject.
Figure 7B:
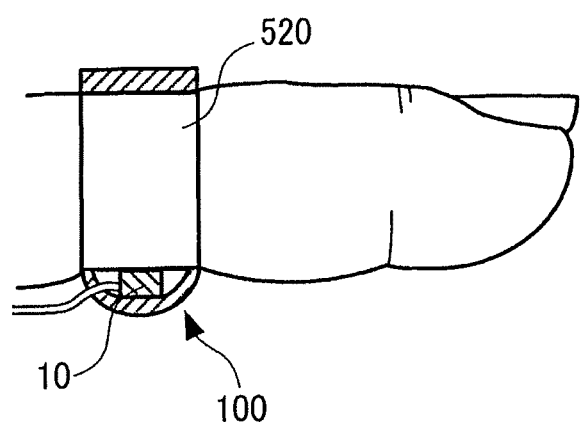

FIGS. 7A and 7B show examples in which the pulsation detection device is worn by the test subject. The example shown in FIG. 7A is an example of a wristwatch-type pulsation detection device. A base part 530 including the pulse wave sensor unit 10 and a display unit 94 is worn on the left wrist 500 of the test subject (user) using a wristband 510.

The example shown in FIG. 7B is an example of a finger-mounted pulsation detection device. The pulse wave sensor unit 10 is provided at a bottom part of a ring-shaped guide 520 to be fitted onto a finger of the test subject.

According to at least one embodiment of the invention, it is possible to, e.g., enhance the filter performance while reducing the processing load on the filter device.

While a detailed description of the present embodiment has been given above, it will be readily apparent to those skilled in the art that numerous modifications can be made without substantially departing from the novel matters and effects of the invention. Consequently, all modifications such as the above can be understood to fall within the scope of the invention. For example, terms disclosed together with different equivalent or broader terms in at least one instance in the specification or drawings can be replaced by these different terms at any place in the specification or drawings.

What is claimed is:

1. A filter device comprising:
    a filter that separates a steady component and a non-steady component included in an input signal, the filter being an adaptive filter in which updating of a filter coefficient causes frequency response characteristics to adapt in an autonomous fashion;
    a synthesis unit that synthesizes the separated steady component and the separated non-steady component according to a given ratio; and
    an evaluation unit that evaluates, on the basis of a result of a frequency analysis performed on at least one of the input signal, the separated steady component, and the separated non-steady component, the magnitude of the amount of the non-steady component included in the input signal; wherein
    the synthesis unit sets the given ratio to a first ratio in an instance in which the evaluation unit determines the amount of the non-steady component to be equal to or less than a predetermined reference, and sets the given ratio to a second ratio, in which the proportion of the non-steady component is less than that of the first ratio, in an instance in which the evaluation unit determines the amount of the non-steady component to be greater than the predetermined reference.

2. The filter device according to claim 1, wherein
    the synthesis unit includes
        a first amplifier that amplifies the steady component by a first gain;
        a second amplifier that amplifies the non-steady component by a second gain; and
        an adder that adds an output of the first amplifier and an output of the second amplifier; wherein
    taking as a first value the value of the first gain when the given ratio is the first ratio, and taking as a second value the value of the first gain when the given ratio is the second ratio,
    the filter device sets the second gain to zero, and uses a value greater than the first value as the second value of the first gain, in an instance in which the given ratio is the second ratio.

3. The filter device according to claim 1, wherein
    when the given ratio is the second ratio, the adaptive filter discontinues updating of the filter coefficient.

4. The filter device according to claim 1, wherein
    if a state in which the amount of the non-steady component is equal to or less than the predetermined reference is maintained over a first period, which lasts until a predetermined time has elapsed from a point in time at which the evaluation unit determines the amount of the non-steady component exceeds the predetermined reference, the filter device returns the given ratio from the second ratio to the first ratio at a point in time at which the first period has elapsed or after the first period has elapsed.

5. The filter device according to claim 3, wherein
    if a state in which the amount of the non-steady component is equal to or less than the predetermined reference is maintained over a first period, which lasts until a predetermined time has elapsed from a point in time at which the evaluation unit determines the amount of the non-steady component exceeds the predetermined reference, the adaptive filter restarts the updating of the filter coefficient at the point in time at which the first period has elapsed or after the first period has elapsed.

6. The filter device according to claim 1, wherein
in the second ratio, the proportion of the non-steady component is zero.

7. The filter device according to claim 1, wherein
the input signal is a pulse wave signal including, as the steady components, a pulsation signal and a body motion component originating from body motion of a test subject; and, as the non-steady component, disturbance noise.

8. The filter device according to claim 7, further comprising
a body motion filter that suppresses the body motion component included in the pulse wave signal.

* * * * *